Figure 1:
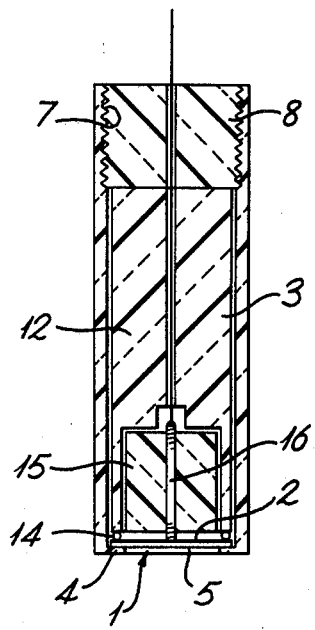

United States Patent [19]

Ebdon et al.

[11] 4,400,243
[45] Aug. 23, 1983

[54] MONITORING OF HEAVY METAL IONS, ELECTRODE THEREFOR AND METHOD OF MAKING A MEMBRANE SENSITIVE TO HEAVY METAL IONS

[76] Inventors: Leslie C. Ebdon, 68 Parkhead Rd., Sheffield S11 9RB; Brendan P. Hafferty, 5 Gaythorne Ter., Clayton, Bradford, Yorkshire, both of United Kingdom

[21] Appl. No.: 396,283

[22] Filed: Jul. 8, 1982

Related U.S. Application Data

[63] Continuation of Ser. No. 201,377, Oct. 27, 1980, abandoned.

[30] Foreign Application Priority Data

Oct. 25, 1979 [GB] United Kingdom ............. 7937132

[51] Int. Cl.$^3$ ................. G01N 27/30; G01N 27/46
[52] U.S. Cl. .................................. 204/1 T; 204/419
[58] Field of Search ................. 204/195 M, 1 T

[56] References Cited

U.S. PATENT DOCUMENTS

| | | | |
|---|---|---|---|
| 3,591,464 | 7/1971 | Frandt et al. | 204/1 T |
| 3,770,608 | 11/1973 | Kelch et al. | 204/195 M |
| 3,824,170 | 7/1974 | Weelink et al. | 204/195 M |
| 3,892,833 | 7/1975 | Hattori et al. | 204/1 T X |
| 3,909,384 | 9/1975 | Jasinski et al. | 204/195 M X |

OTHER PUBLICATIONS

Durst, Richard A., "Ion-Selective Electrodes", pp. 79-81, (1969).

*Primary Examiner*—G. L. Kaplan
*Attorney, Agent, or Firm*—Oblon, Fisher, Spivak, McClelland & Maier

[57] ABSTRACT

A metal sulphide ionic membrane for use in monitoring heavy metal ions in solution comprises a mixture of at least four metal sulphides in relative proportions such that the membrane is capable of responding electrochemically to all of the corresponding metal ions when said ions are contained in solution, e.g. at concentrations in the range from $10^{-5}$ up to 1M. A preferred embodiment of the ionic membrane consists of a mixture of silver 15 to 65% by weight, cadmium 15 to 65% by weight, lead 30 to 65% by weight and copper 3 to 9% by weight sulphides. The ionic membranes are preferably prepared by co-precipitation of sulphides followed by hot pressing and may be detachably mounted in suitable electrodes, internal electrical connections made either by way of filling solutions or by direct connection, preferably biassed connection, of an internal conductor to the internal surface of the electrode pellet.

16 Claims, 6 Drawing Figures

MONITORING OF HEAVY METAL IONS, ELECTRODE THEREFOR AND METHOD OF MAKING A MEMBRANE SENSITIVE TO HEAVY METAL IONS

This is a continuation of application Ser. No. 201,377 filed Oct. 27, 1980 and now abandoned.

This invention relates to the monitoring of heavy metal ions and in particular to an electrode system for monitoring the presence in solution of the heavy metal ions silver, cadmium, lead and copper.

It is highly desirable to be able to monitor the presence of heavy metal ions in industrial effluents, such as electroplating effluents, as the loss of heavy metal ions in solution may present a serious economic loss let alone a considerable hazard to the environment. Ion-selective electrodes may be used for monitoring the heavy metal ions, and such ion-selective electrodes typically comprise an ionic membrane which responds selectively to the specific metal ion which it is desired to monitor. Amongst the various ionic membranes which may be used in ion-selective electrodes for monitoring heavy metal ions, membranes comprising metal sulphide have been used for monitoring corresponding metal ions in solution. Hitherto such metal sulphide ionic membranes have comprised a mixture of up to three metal sulphides: predominantly silver sulphide (often up to about 90% by weight of the membrane) to provide the required electrical conductance properties, together with a small proportion (e.g. about 5% by weight) of copper sulphide to give the membrane desirable physical properties, the remainder of the membrane being made up of the sulphide of the metal which it is desired to monitor. Such three component metal sulphide ionic membranes are intended for use in ion-selective electrodes for the selective monitoring of ions of a single metal only.

The present invention arises from consideration of the real needs of a heavy metal ion monitor which has led to a fundamental re-appraisal of the requirements of ionic membranes for electrodes for use in the monitoring of such ions in solutions, such as effluents. Thus the invention provides an ionic membrane which is capable of responding to a plurality of different metal ions, such that it is adapted for use in the monitoring of the sum total of all of these metal ions present in solution.

According to the present invention a metal sulphide ionic membrane comprises a mixture of at least four metal sulphides in relative proportions such that the membrane is capable of responding electrochemically to all of the corresponding metal ions when said ions are contained in solution.

The invention also includes an ion-monitoring electrode for monitoring the corresponding metal ions in solution which comprises a metal sulphide ionic membrane according to the present invention. Furthermore the invention includes methods of monitoring the sum total of a plurality of metal ions in solution which comprises monitoring the e.m.f. produced in a cell containing an ion-monitoring electrode according to the invention.

The metal sulphides and their relative proportions present in the ionic membrane of the invention may be varied as required to give the desired performance. Thus the membrane may comprise a mixture of sulphides of heavy metals including mercury, zinc and nickel, and in particular silver, cadmium, copper and lead. Preferably the relative proportions of the various sulphides are such that the membrane is capable of responding electrochemically to each of the various metal ions when these are in solution in a preferred concentration range from $10^{-5}$ up to 1 molar, e.g. at least up to $10^{-1}$ molar, though it will be appreciated that the relative proportions of the sulphides may be adjusted so that the ionic membrane is capable of responding to specific metal ions at concentrations outside the preferred range. For instance, it may be desired to monitor some metal ions, e.g. mercury, at concentrations below $10^{-5}$ molar in view of statuory effluent control requirements.

In a preferred embodiment the ionic membrane composition of the present invention consists of a mixture of silver, cadmium, lead and copper sulphides, usually containing from 15 to 65% by weight of each of silver and cadmium sulphides, from 30 to 65% by weight of lead sulphide and from 3 to 9% by weight of copper sulphide. Preferably the composition of such a silver, cadmium, lead and copper sulphide ionic membrane consists of from 20 to 55% by weight of each of silver and cadmium sulphides, from 35 to 55% by weight of lead sulphide and from 5 to 8% by weight of copper sulphide. In a particularly preferred embodiment of the four component silver, lead, cadmium and copper sulphide ionic membrane, the proportions of each of the silver and cadmium sulphide components present in the membrane are about 25% by weight, e.g. $Ag_2S$ 23% and Cd S 26.8%, the proportion of lead sulphide is about 45% by weight, e.g. 44.5% and the proportion of copper sulphide is about 5% by weight, e.g. 5.9%.

The metal sulphide ionic membranes of the invention are prepared by mixing at least four metal sulphides together and fabricating the resultant mixture into the membrane, the relative proportions of the metal sulphides being such that the resultant membrane is capable of responding electrochemically to all of the corresponding metal ions when said metal ions are in solution. The mixture of sulphides for fabrication of the ion-selective membranes of the invention, which is typically in finely divided and preferably intimately mixed form, may be prepared by any suitable technique, though co-precipitation of the metal sulphides is particularly preferred. For example, solutions of the various metal ions, e.g. nitrate solutions, are treated with sulphide to co-precipitate the sulphide mixture.

The requisite sulphide mixture, whether prepared by co-precipitation or otherwise, may be fabricated into an ionic membrane, usually by a pressing technique. Fabrication of the sulphide mixture into the membrane may also include heat treatment, particularly when the sulphide mixture comprises silver sulphide, heat treatment, e.g. to a temperature of at least about 180° C., bringing about a desirable phase change which opens up the structure of the silver sulphide enhancing the intimate mixing of the components. Preferably heat treatment may be carried out during pressing, i.e. ionic membrane electrolyte pellets are prepared by hot pressing techniques. For instance, the ionic membrane is fabricated by hot pressing at temperatures from about 100° up to about 200° C., preferably about 150° C. under a pressure of from about 20 up to about 80 tons per square inch, preferably about 60 tons per square inch for a period of from about 2 hours up to about 8 hours, preferably about 4 hours.

After fabrication, the surface of the ionic membrane, usually in the form of an electrode pellet, is preferably polished prior to use which advantageously enhances the electrochemical response characteristics of the membrane. The electrode pellet may be mounted in any suitable electrode configuration, preferably in a replaceable mounting so that the ionic membrane may be replaced if it becomes defective. For example, the electrode pellet is mounted, preferably replaceably mounted, in one end of a tubular electrode body. The electrode is typically provided with means for making an internal electrical connection, and this may be effected by way of a suitable internal filling solution. For example, a suitable internal filling solution suitable for use with a silver sulphide/cadmium sulphide/lead sulphide/copper sulphide electrode comprises cadmium chloride (e.g. 0.1 mol. $dm^{-3}$), copper nitrate (e.g. 0.001 mol. $dm^{-3}$) and sodium chloride (e.g. 0.01 mol. $dm^{-3}$), saturated with silver chloride. Preferably, however, the internal electrical connection of the electrode is made by direct connection of an internal conductor to the internal surface of the electrode pellet. For instance, an internal conductor, e.g. a silver wire, is attached directly to the internal surface of the electrode pellet by means of a conducting adhesive, e.g. a silver containing adhesive. In a preferred direct connection arrangement, the end of an internal conductor is not fixed to but is held against the internal surface of the electrode pellet, usually by a biassing means such as a spring, and the internal surface of the pellet is coated with a suitable conducting medium, e.g. a thermo-setting silver epoxy resin. Such a biassed, non-fixed, direct internal connection advantageously permits replacement of the electrode pellet.

The electrode of the invention may be used in combination with any suitable reference electrode, such as a standard calomel electrode.

The e.m.f. produced by the electrode of the invention may be monitored to give a quantitative indication of the combination of metals present in solution. Preferably, however, the e.m.f. from the electrode is channelled to a suitable switching device, such as a relay, such that when the e.m.f. rises above a predetermined level it operates the switching device, for instance, to set off an alarm or initiate some other activity as required. In this fashion the electrode of the invention may be used to monitor the presence of a combination of metal ions in effluent streams, either constantly or intermittently, and thereby give rapid warning of undesirable release of heavy metals into the effluent stream, so that suitable corrective action may be taken at an early stage.

In a preferred embodiment the invention also includes a flow cell for use with the electrode of the invention. This flow cell essentially comprises a liquid passageway having two interconnecting compartments through which liquid sampled from a liquid stream, such as an effluent stream, is passed. The flow cell comprises a first compartment provided with means for mounting a reference electrode in a liquid stream, and connected therewith a second compartment with means for mounting a monitoring electrode in the liquid stream. Characteristically, the liquid flow through the two compartments is arranged so that a jet of liquid is directed on to the surface of the electrolyte membrane of the monitoring electrode. In a preferred embodiment, the liquid flow is directed by the passageway between the two compartments to form a high speed jet of liquid against the electrolyte membrane. In this regard, a connecting passageway of about 2 mm in diameter has been found to be suitable when a flow rate of about 50 ml per minute is used. The jet stream which is directed against the electrolyte membrane advantageously provides a cleaning action for the surface of the membrane and also prevents the trapping of air bubbles against the external surface of the membrane, e.g. when the surface of the membrane is recessed into the end face of the electrode as in an electrode having a replaceable electrolyte membrane.

Preferably the flow cell compartments are of relatively small volume and are in relatively close proximity, such that both electrodes experience substantially the same liquid environment. Preferably also, the liquid inlets and outlets of the compartments are located such that when the flow cell is in use a liquid layer is maintained over the surface of the reference electrode, to advantageously prevent the reference electrode from drying out. For instance, the liquid outlet to the monitoring electrode compartment is located above the level of the reference electrode when the flow cell is in use.

In practice, when using a flow cell in combination with the electrode of the invention, it has been found to be desirable to control the temperature of the flowing liquid stream within close limits, e.g. at 20°±1° C. Preferably, therefore, the flow cell is thermostatted as desired, and for this purpose the flow cell may be encased within a suitable temperature stable environment such as a thermosetted metal block. Preferably the liquid stream which is passed into the flow cell is thermostatted in a suitable heat exchanger prior to introduction to the flow cell, and this heat exchanger may be included within the thermostatted enclosure for the flow cell.

Figure 2:
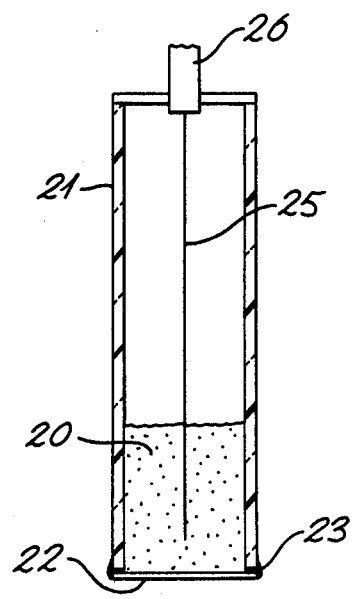
Figure 3:
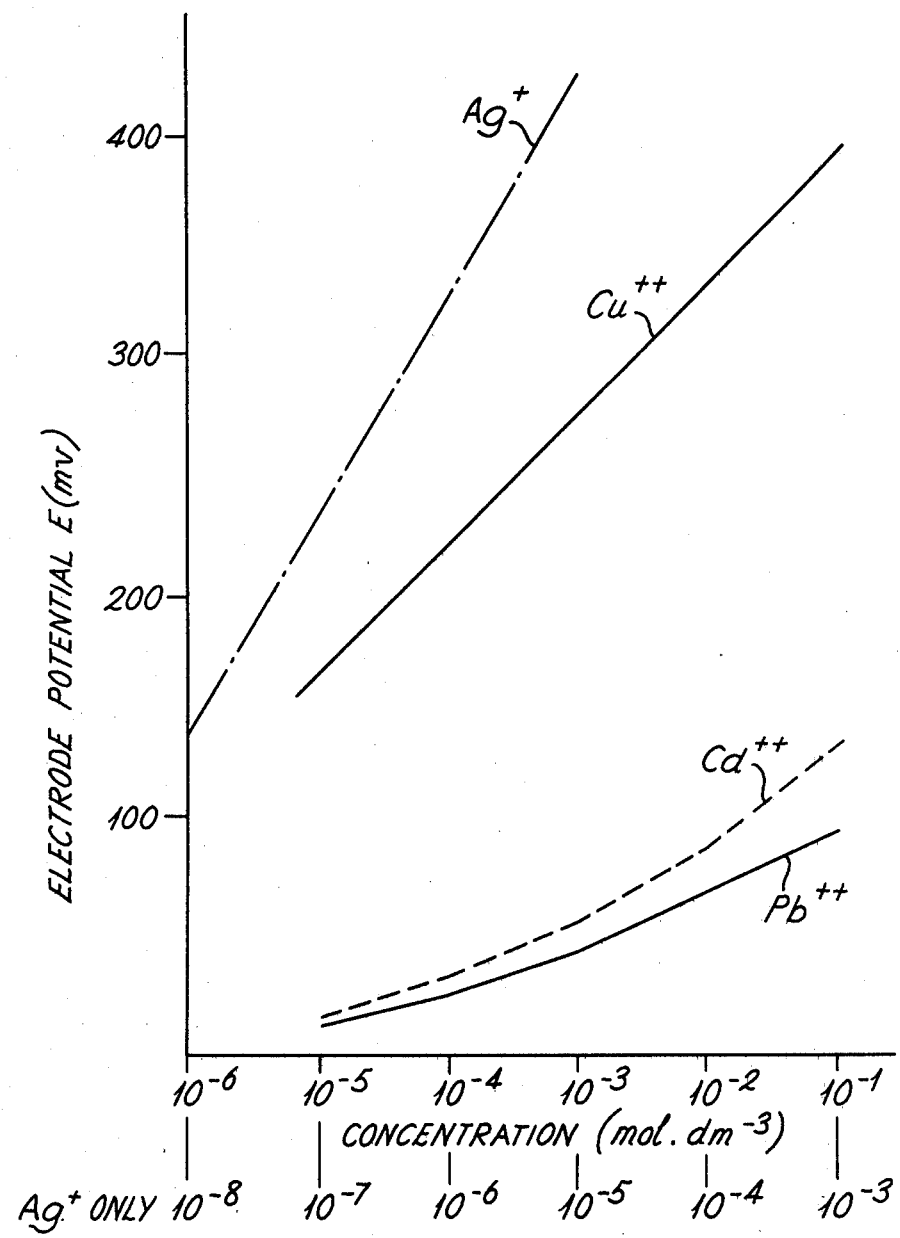
Figure 4:
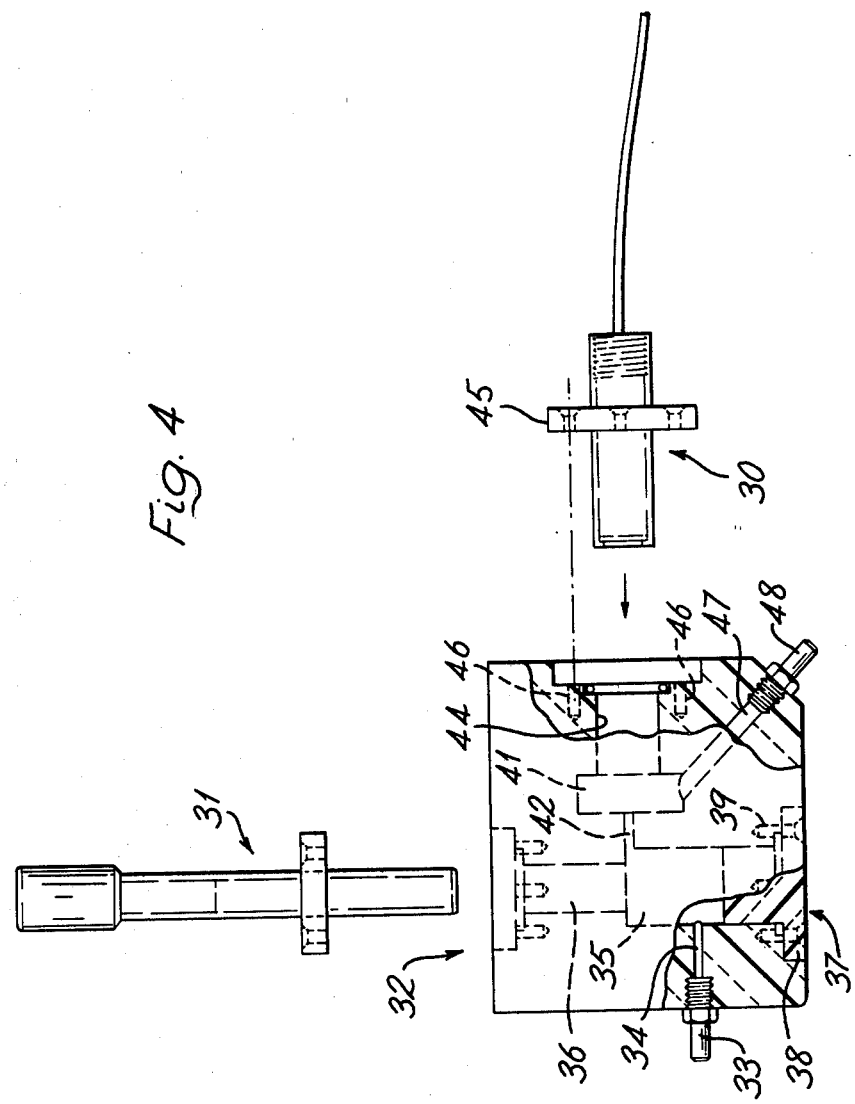
Figure 5:
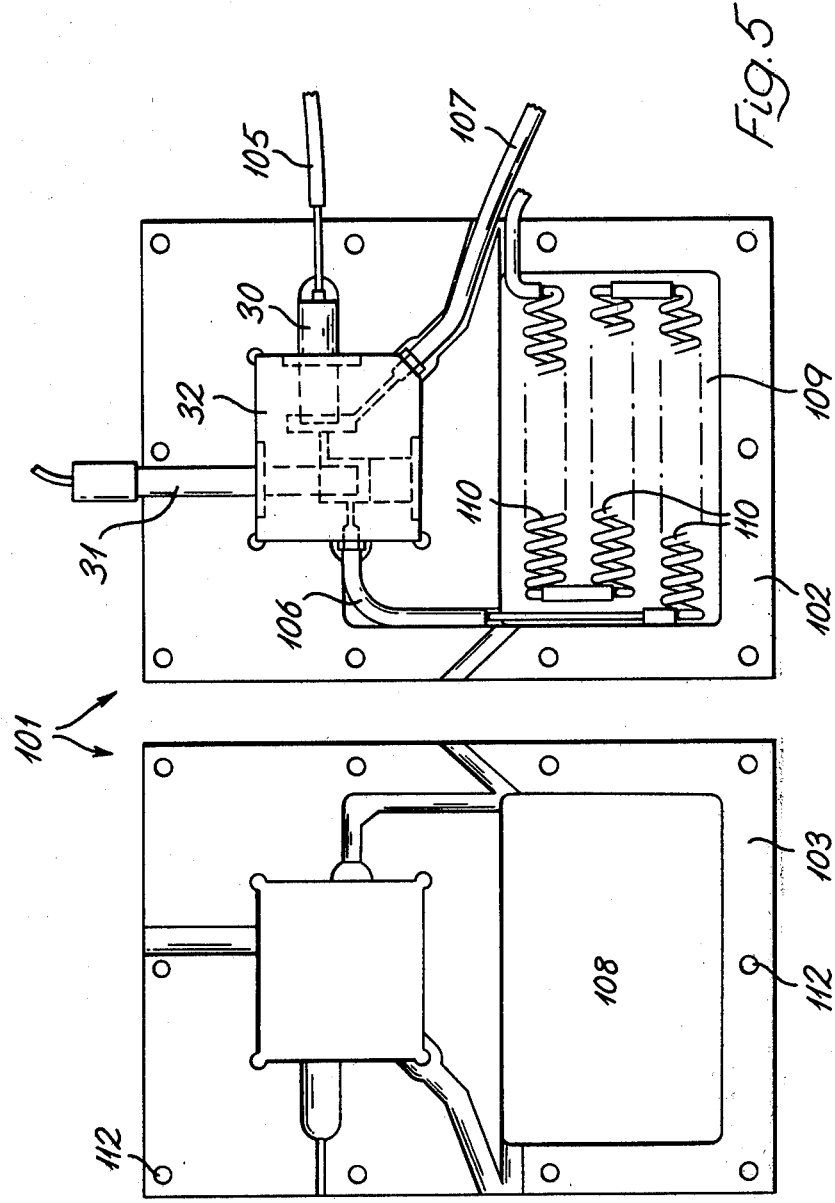
Figure 6:
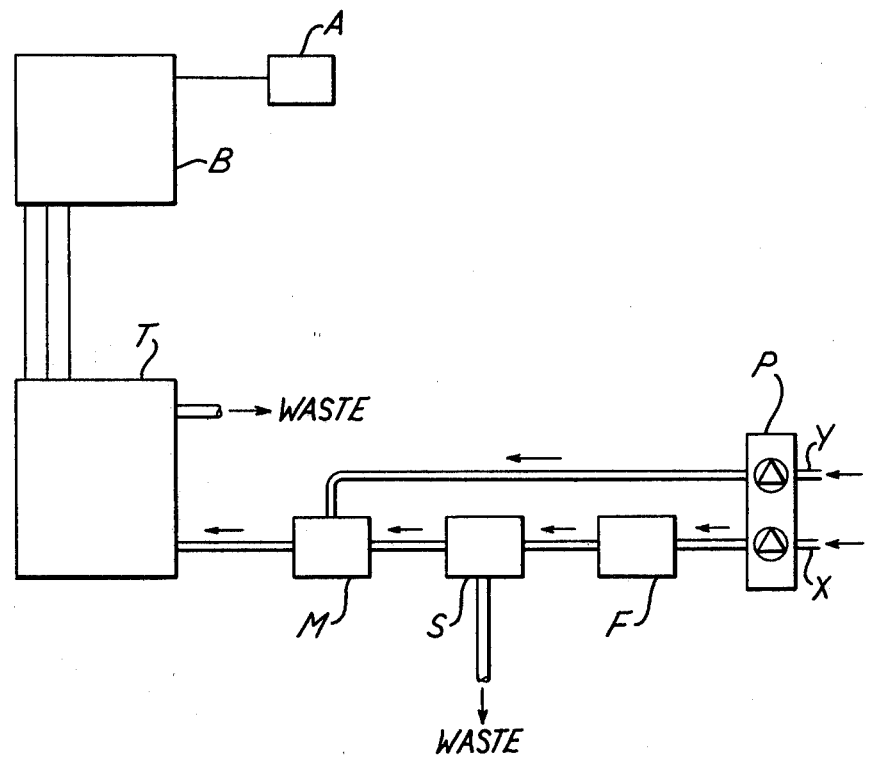

The present invention is further described by way of illustration only in the following description which refers to the accompanying diagrams:

FIG. 1 which shows a sectional view of a direct internal connection electrode according to the invention, the section taken along the axis of the electrode;

FIG. 2 which shows a similar view of an electrode according to the invention in which internal connection is made by way of a filling solution;

FIG. 3 which shows calibration curves for the electrode of FIG. 1;

FIG. 4 which shows an exploded elevation view of a flow cell according to the invention;

FIG. 5 which shows a view of the flow cell of FIG. 4, in diminished scale, in place within one plate of a heat exchanger block, and FIG. 6 is a schematic diagram of a heavy metal ion monitor.

CO-PRECIPITATION OF HEAVY METAL SULPHIDE MIXTURE

A mixture of heavy metal sulphides, cadmium sulphide, lead sulphide, silver sulphide and copper sulphide, is prepared by co-precipitation of the sulphides from a mixed solution of the nitrate salts (Analar grade). A mixed solution of the nitrates is made up in de-ionised water, well stirred and kept at or near 0° C. in an ice bath, the solution containing cadmium nitrate (0.3 mol. $dm^{-3}$) lead (II) nitrate (0.3 mol. $dm^{-3}$) silver nitrate (0.3 mol. $dm^{-3}$) and copper (II) nitrate (0.1 mol. $dm^{-3}$). A solution of sodium sulphide (1.0 mol. $dm^{-3}$), analar grade reagent in de-ionised water is also prepared and kept at or near 0° C. in an ice bath. The nitrate solution (x$cm^3$) is then rapidly added to the sulphide solution (1.5 x$cm^3$) with constant stirring and the temperature is maintained below 20° C. during mixing.

The resultant black co-precipitate of mixed sulphides is then washed and dried as follows:
(1) wash with at least 500 cm³ cold de-ionised water,
(2) allow to settle and pour supernatant liquid off,
(3) wash with 500 cm³ of hot (60° C.) de-ionised water,
(4) filter through a grade 3 sinter filter,
(5) wash with 100 cm³ of dilute (2 mol. dm⁻³) nitric acid for a short period,
(6) filter again until dry,
(7) wash with 250 cm³ carbon disulphide (Analar grade),
(8) filter until dry,
(9) wash with 500 cm³ de-ionised water,
(10) filter until dry,
(11) wash with 200 cm³ acetone,
(12) filter until dry,
(13) dry overnight in a vacuum desiccator in the dark,
(14) grind to a fine powder in an agate mortar with an agate pestle,
(15) store, if required, in a brown-coloured, air-tight, glass container.

Preparation of ion-selective membrane 200 mg of the finely ground sulphide mixture is weighed out and introduced into a stainless steel die (internal diameter 13 mm). The die is placed in the centre of an electrically heated element enclosed in a thermally insulated five-sided box which is open at the top. The complete pressing unit is then placed in a standard hydraulic press and the ram brought into location on to the top of the piston of the die. The heating element is then switched on and adjusted by means of a variable resistor, the temperature of the powder being ascertained by means of a thermocouple previously introduced into the die. When the temperature reaches the desired level (150° C.) the hydraulic ram is activated, the pressure being increased upon the piston of the die up to a level not greater than 80 tons per square inch. After 4 hours the heating unit is switched off coincident with the release of pressure on the ram. The resultant pellet, which is 13 mm in diameter and approximately 1 mm in thickness, is released from the die whilst the die is still reasonably hot.

Both surfaces of the pellet are polished with a fine polishing powder (U.M.P.A. Gamma grade) until a mirror finish is achieved. The polished membrane is then ready to be mounted within the electrode body.

Membrane mounting and electrical connection

Connection of the inner membrane surface to a high impedance millivoltmeter, for monitoring the variations in electrode potential, may be achieved by means of a dry wired connection or by use of a filling solution.

(A) Dry wired connection: with reference to FIG. 1 the polished membrane 1 is coated on its inner face with a thin layer 2 of thermo-setting silver epoxy resin and the membrane is mounted in one end of a tubular perspex electrode body 3 against an inturned annular shoulder 4, the polished surface 5 of the membrane being exposed to the outside through a hole in the end of the electrode body. The other end of the electrode body is internally threaded 7 to receive in screw threaded engagement a threaded plastic spacer 8 having an oversized axial bore therethrough for accommodating an electrically conducting wire 10. The spacer 8 bears on one end of a cylindrical spacer 12 which is a loose fit within the electrode body and bears on its other end against an O-ring 14 which holds the membrane 1 in position against the inturned shoulder 4. The spacer 12 similarly has an oversized axial bore for accommodating the conducting wire 10, and at the membrane end thereof has a cylindrical recess for accommodating a spring connector holder 15 accommodating along its axis a gold flashed spring connector 16 which when held against the internal surface of the membrane 1, as shown in FIG. 1, completes the electrical connection between the conducting wire 10 and the internal surface of the membrane.

(B) Internal filling solution electrode: with reference to FIG. 2 an alternative form of electrode comprises an internal filling solution consisting of a solution in de-ionised water of cadmium chloride ($6.5 \times 10^{-2}$ mol. dm⁻³), silver nitrate ($3.3 \times 10^{-4}$ mol. dm³¹ ³) and copper nitrate ($3.3 \times 10^{-4}$ mol. dm⁻³). The filling solution 20 is enclosed within a tubular perspex electrode body 21 closed at one end by a sensor membrane 22 which is attached to the end of the perspex tube by means of an epoxy resin adhesive 23. A silver/silver chloride coated wire internal reference electrode 25 extends from an insulated connector 26 located in the opposite end of the tubular electrode into the filling solution 20.

Calibration of hardwired electrode

The hardwired electrode of FIG. 1, as described above, is calibrated for response to silver, copper (II), cadmium and lead ions by introduction into solutions of known concentration of each metal ion in turn, the potential of the electrode being noted against that of a double junction Ag/AgCl reference electrode. The results obtained are given in FIG. 3 which shows that the electrode responds adequately to all four ions, though especially well to silver and copper ions.

Flow cell

With reference to FIG. 4 the dry wired electrode 30, as shown in detail in FIG. 1, is used together with a calomel reference electrode 31 in a flow cell 32 comprising a rectangular block of perspex material having a liquid flow passage therethrough. The fluid passageway has an inlet provided through one end of the perspex block 32 by a tubular plastic boss 33 located in a screw threaded recess, the passageway extending therefrom by means of a drill hole 34 into a first compartment 35 for accommodating the reference electrode 31. The cylindrical compartment 35 communicates co-axially through the top of the block 32 with the exterior by way of a borehole 36 which is a tight fit for the body of the reference electrode 31 and which is sealed thereby when the electrode 31 is introduced to the compartment 35. The lower end of the compartment 35 also communicates with the exterior through the bottom of the block 32, though as shown in FIG. 4 is closed by means of a perspex plug 37 having an enlarged head portion 38 which is held in a corresponding recess in the bottom of the block 32 by three screws 39. This plug 37 may be removed on undoing the screws 39 to permit access to the interior of the compartment 35 for cleaning.

The reference electrode compartment 35 communicates with a disc-shaped sensor compartment 41 by way of a narrow (2 mm) drill hole 42 which is coaxial therewith. The compartment 41 communicates with the exterior through the end of the block 32 by way of a coaxial bore hole 44 which is a tight fit for the body of the sensor electrode 30 and is sealed thereby when the electrode 30 is introduced to the compartment 41. The electrode 30 has a coaxial flange 45 around its body which locates in an enlarged recess surrounding the opening of the bore hold 44 in the end of the block 32, and which provides means for fixedly locating the electrode 30 in the bore hole 44 by means of screws (not shown) which pass through the flange 45 and locate in screw threaded recesses 46. The compartment 41 is provided with a fluid outlet by means of an intermediate size bore hole 47 which extends downwards at an oblique angle from the bottom of the compartment 41 exiting from the block 32 through a tubular plastic boss 48 located in screw threaded engagement in a chamfer in the corner of the block 32.

Liquid flowing through the flow cell 32 enters via the tubular boss 33 into the first reference electrode compartment 35 where it contacts the reference electrode 31. From here the liquid flows via the narrow tubular passageway 42 into the monitoring electrode compartment 41 the liquid stream impinging directly on the surface of the electrolyte pellet of the sensor electrode 30, thereby cleaning and preventing the trapping of bubbles against the electrolyte membrane. From the compartment 41 the liquid flows from the cell via the bore hole 47 and tubular boss 48. The passage 42 is located above the level of the reference electrode 31 when the cell is in use and thereby ensures that a layer of liquid remains covering the reference electrode 31, preventing it from drying out, if the liquid flow is stopped.

Temperature Control Block

With reference to FIG. 5, the perspex flow cell 32, as described above with reference to FIG. 4, is located in a metal temperature control block 101 during use. The temperature control block comprises four metal plates only two of which, plates 102 and 103, are shown providing the inner pair of a four plate sandwich when in use. Plate 103 and its corresponding outer plate (not shown) are split in two parts so that either of the two halves of the system can be explosed selectively without exposing the other half, for instance for maintenance. The upper halves of plates 102 and 103 are suitably machined on their adjacent faces to accommodate the flow cell 32, sensor 30 and reference 31 electrodes, electrical connections 105 therefor and fluid flow tubes 106 and 107 for connection to the tubular inlet and outlet 48 bosses of the flow cell. Below the flow cell recesses are provided rectangular recesses 108 and 109 for accommodating three helical mixing and heat exchange coils 110 through which liquid flow entering the control block 101 is passed for equilibration of temperature before the liquid is passed into the flow cell via tube 106. Temperature control is achieved by filling with oil the chamber, produced when the lower halves of plates 102 and 103 are bolted together, and providing thermostatted heating by means of heating mats (not shown), ca. 9 cm by 4 cm, sandwiched between the outer faces of plates 102 and 103 and their corresponding outer metal plates (not shown).

Heavy metal ion monitor

With reference to FIG. 6, the electrode, flow cell and temperature control block described above are incorporated in a heavy metal ion monitor. A liquid stream X is sampled by means of a peristaltic pump P, filtered and aliquots drawn off by means of a stream splitter S and mixed with buffer solution (liquid stream Y also supplied from the peristaltic pump P) in a mixing unit M. The buffered sample stream is then passed into a temperature control unit T containing a flow cell fitted with an electrode according to the invention. From the unit T the liquid flow is passed to waste. Electronic signals developed by the sensor electrode are passed to an electronic module B containing circuitry for a high impedance amplifier, a temperature control for the unit T and alarm level switching capabilities. When the e.m.f. generated by the sensor electrode rises above a predetermined level as the result of an unwanted release of heavy metal ions in the liquid sample, an alarm unit A, e.g. bell, light or other suitable alarm means, is activated.

We claim:

1. A metal sulfide ionic membrane composition, comprising:
    a mixture of at least four metal sulfides, said sulfides being 15–65% by weight silver sulfide, 15–65% by weight cadmium sulfide, 30–65% by weight lead sulfide, and 3–9% by weight copper sulfide, such that the membrane is capable of responding electrochemically to all of the corresponding metal ions when said ions are present in solution.

2. A method for the production of the metal sulfide membrane of claim 1, comprising:
    mixing at least four of said metal sulfides in said proportions such that the resultant membrane is capable of responding electrochemically to all of the corresponding metal ions when said metal ions are present in solution; and
    shaping the mixture into a membrane.

3. The method of claim 2, wherein the sulfides in mixed and finely divided form are prepared by coprecipitation from solution.

4. The method of claim 2, which comprises:
    hot pressing said mixed sulfides to shape said mixture into a membrane.

5. The method of claim 4, wherein said hot pressing step is conducted at a temperature from about 100° up to about 200° C. under a pressure of from about 20 up to about 80 tons per square inch for a period of from 2 hours up to about 8 hours.

6. The method of claim 2, wherein the surface of the membrane is polished prior to use.

7. The metal sulfide ionic membrane composition of claim 1, wherein said membrane comprises 20–55% by weight silver sulfide, 20–55% by weight cadmium sulfide, 30–55% by weight lead sulfide, and 5–8% by weight copper sulfide.

8. The metal sulfide ionic membrane composition of claim 7, wherein said membrane comprises 25% by weight silver sulfide, 25% by weight cadmium sulfide, 45% by weight lead sulfide, and 5% by weight copper sulfide.

9. An electrode for monitoring metal ions in solution comprising the metal sulfide membrane of claim 1, 2 or 3.

10. The electrode of claim 9, wherein said shaped membrane is in the form of a pellet secured in said electrode by a replaceable mounting.

11. The electrode of claim 9, wherein said pellet is mounted in one end of a tubular electrode body.

12. The electrode of claim 9, in which internal electrical connection is effected by way of an internal filling solution.

13. The electrode of claim 9, in which internal electrical connection is effected by way of direct connection of an internal conductor to the internal surface of said pellet.

14. The electrode of claim 13, in which the internal connector is not fixed but is held against the internal surface of the pellet by a biasing means.

15. A method for monitoring a combination of metal ions present in solution, which comprises: monitoring the e.m.f. generated in a cell containing the electrode of claim 9.

16. The method of claim 15, in which the e.m.f. generated in a cell containing the electrode is channeled to a switching device.

* * * * *